United States Patent [19]
Rosenberg

[11] Patent Number: 5,425,760
[45] Date of Patent: Jun. 20, 1995

[54] TISSUE EXPANDER APPARATUS, AND METHODS OF CONSTRUCTING AND UTILIZING SAME

[76] Inventor: Paul H. Rosenberg, 1320 York Ave., Apt. 23N, New York, N.Y. 10021

[21] Appl. No.: 285,490
[22] Filed: Aug. 3, 1994

Related U.S. Application Data

[63] Continuation of Ser. No. 878,161, May 4, 1992, abandoned.

[51] Int. Cl.⁶ .................................................. A61F 2/12
[52] U.S. Cl. ...................................... 623/8; 606/192; 128/899
[58] Field of Search ............................ 604/96–103; 606/191–195; 623/1, 8, 11; 128/899

[56] References Cited

U.S. PATENT DOCUMENTS

| | | |
|---|---|---|
| 4,157,085 | 6/1979 | Austad . |
| 4,574,780 | 3/1986 | Manders . |
| 4,685,447 | 8/1987 | Iversen et al. . |
| 4,800,901 | 1/1989 | Rosenberg . |
| 4,817,637 | 4/1989 | Hillegass et al. . |
| 4,840,615 | 6/1989 | Hancock et al. . |
| 4,841,992 | 6/1989 | Sasaki et al. . |
| 4,955,395 | 9/1990 | Manders . |
| 5,002,531 | 3/1991 | Bonzel ................................ 604/96 |
| 5,005,591 | 4/1991 | Austad . |
| 5,083,576 | 1/1992 | Ruiz-Razura et al. ............. 604/96 |
| 5,141,494 | 8/1992 | Danforth et al. ................... 606/194 |
| 5,147,377 | 9/1992 | Sahota ................................ 606/96 |
| 5,258,026 | 11/1993 | Johnson et al. . |

OTHER PUBLICATIONS

Brochure of the American Society of Plastic and Reconstructive Surgeons, Inc. Entitled "Tissue Expansion, Creating New Skin From Old" Copyright 1988.

*Primary Examiner*—Stephen C. Pellegrino
*Assistant Examiner*—William Lewis
*Attorney, Agent, or Firm*—Cohen, Pontani, Lieberman, Pavane

[57] ABSTRACT

A tissue expander device is provided which permits insertion at a significant distance from the area to be expanded, preferably hidden in a skin crease or in some other inconspicuous place. A central removable firm member is disposed within the expanded device to facilitate subcutaneous passage from an insertion site to a remote tissue expansion site.

18 Claims, 1 Drawing Sheet

TISSUE EXPANDER APPARATUS, AND METHODS OF CONSTRUCTING AND UTILIZING SAME

This is a continuation, of U.S. application Ser. No. 07/878,161, filed May 4, 1992 now abandoned.

BACKGROUND OF THE INVENTION

The invention relates to a tissue expander apparatus and tissue expansion methods enabling insertion at an insertion site which is remote from a tissue expansion site.

The invention permits remote subcutaneous insertion of a balloon-like tissue expander to eliminate currently-experienced difficulties with, for example, scar tissue and the like which results when an incision is made at or near the location where the tissue expander is to be placed. None of the art teaches or suggests remote subcutaneous insertion of a tissue expander, nor the novel expander apparatus of the invention.

SUMMARY OF THE INVENTION

The invention provides a tissue expansion method comprising the steps of inserting a substantially firm first device at an insertion site which is remote from a tissue expansion site; passing said first device subcutaneously from said insertion site to said tissue expansion site; withdrawing said first device; inserting a deflated tissue expander device at said insertion site; passing at least an inflatable portion of said deflated tissue expander device subcutaneously from said insertion site to said tissue expansion site; and inflating said inflatable portion of said tissue expander device to expand tissue at said tissue expansion site.

Another version of the invention provides a tissue expansion method comprising the steps of inserting at an insertion site which is remote from a tissue expansion site a tissue expander assembly comprising a deflated tissue expander device and one or more removable substantially firm members; passing said tissue expander assembly subcutaneously from said insertion site to said tissue expansion site; withdrawing said one or more substantially firm members; and at least partially inflating an inflatable portion of said tissue expander device to expand tissue at said tissue expansion site.

The invention also provides a tissue expansion apparatus comprising an inflatable balloon adapted to be passed subcutaneously from an insertion site to a tissue expansion site which is remote from said insertion site; an inflation tube having one end connected to said inflatable balloon and another end serving as an entry port for inflation fluid; a first elongated substantially firm member disposed within said inflation tube and inflatable balloon to facilitate subcutaneous passage of said tissue expander apparatus from said insertion site to said remote tissue expansion site; and said elongated substantially firm first member being adapted to be withdrawn from said inflation tube and inflatable balloon after said inflatable balloon has been positioned at said tissue expansion site and prior to inflation of said inflatable balloon by said inflation fluid.

Further features and advantages of the invention will be apparent from the description below.

DETAILED DESCRIPTION OF PREFERRED EMBODIMENTS

Figures 1, 2:
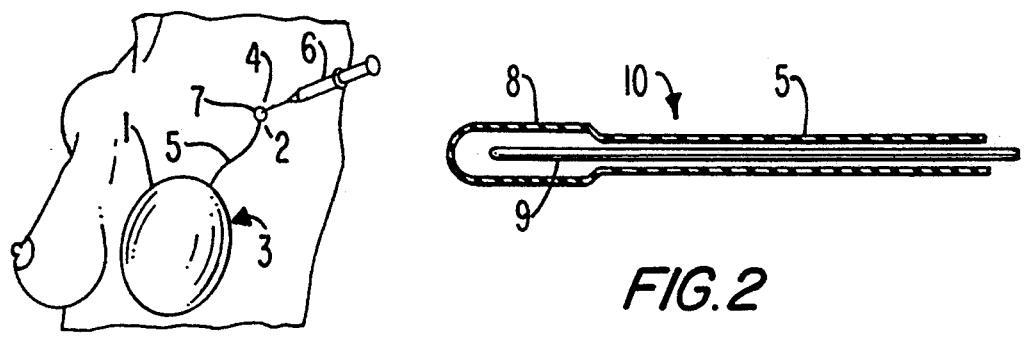
FIG. 1 illustrates the invention showing an insertion site remote from a tissue expansion site.
FIG. 2 shows an enlarged cross-section of a first embodiment of the tissue expander apparatus having a central firm device therein.

The drawings are for illustrative purposes only; to merely show the components. Proportions, dimensions, and spaces in the drawings are not critical; may be ignored where necessary; are used primarily to clearly show arrangement of components.

With reference to FIG. 1, the invention provides a tissue expander apparatus at an insertion site 2 which is remote from a tissue expansion site 3, i.e., a region of soft tissue and skin to be expanded.

Conventionally, a skin incision is made at the peripheri of the area where expansion is desired, followed by placement of an inflatable rubber or silicone balloon in the pocket created by the local dissection. The wound is allowed to heal for several weeks, and subsequently, saline is injected into the balloon via a self-contained or remote injection port at intervals at approximately one week. When expansion is maximal (usually six to ten weeks), the expander is removed and the redundant skin and soft tissue is rotated to an adjacent area to cover a defect, burn, or other deformity.

The major disadvantages of the conventional technique is that the original incision made by the surgeon to place the expander dictates incision in this area once again upon expander removal, and therefore limits the options for eventual rotation of tissue following expansion. Furthermore, because a healing interval is mandatory prior to commencement of expansion, much time is wasted. Also, the volume of saline which may be infused at each office visit is limited by the inherent weakness of the healing surgical wound, again delaying eventual full tissue expansion and final reconstruction.

According to the present invention, the device is inserted at an insertion site 2 located at a considerable distance from the area 3 to be expanded. Preferably, the insertion site 2 is hidden in a skin crease or in some other inconspicuous place 4. A small skin incision is made at the insertion site 2, only large enough to accommodate insertion of the device. Then, a substantially firm first device, such as a firm probe, cannula or sound, is inserted and passed easily in the subcutaneous plane to the region 3 where expansion is desired. The probe is then withdrawn, and the tissue expander device is inserted. After securing the inflation tube 5 at the exit wound at the insertion site 2, a syringe 6 or other inflation device is attached to the insertion port 7 and saline or any other suitable inflation fluid may be immediately infused.

The balloon 8 at the tip of the device inflates, and the skin and soft tissue are expanded. With the present invention, this can be done without delay because there is no incision at the tissue expansion site 3 or at the margin of the tissue expander. The sequential saline infusion may then be carried out, and with the possible accommodation of greater volumes. Once fully expanded, the device is deflated and withdrawn. The surgeon may then decide how and where to incise the redundant tissue to gain maximal benefit from the reconstruction.

FIG. 2 shows a cross-section of a first embodiment. The figure is only for illustrating the elements, and is not for purposes of dimensions.

FIG. 2 shows an inflation tube 5 having at one end thereof a deflated tissue expander balloon 8. An elongated firm device or member 9 is shown centrally disposed within tube 5 and balloon 8. Member 9 aids in the subcutaneous passage of the tissue expander apparatus 10 from insertion site 2 to the remote tissue expansion site 3. After the balloon 8 has been positioned properly at the tissue expansion site 3, the member 9 is removed prior to inflation of the balloon 8.

Figures 3, 4:
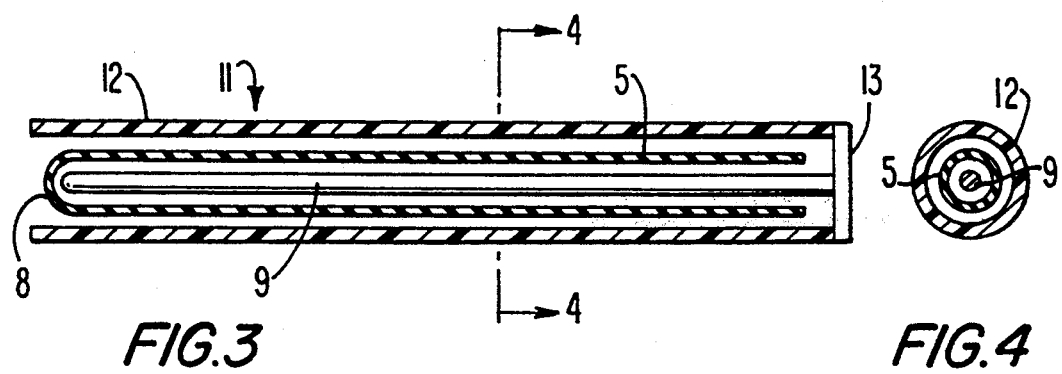
FIG. 3 is an enlarged cross-section of a second embodiment of the tissue expander apparatus.
FIG. 4 shows a transverse cross-section of the FIG. 3 apparatus.

FIG. 3 shows another embodiment in the form of a tissue expander apparatus 11 which shows a first elongated firm member 9 centrally disposed within tube 5 and balloon 8. An outer elongated second firm member 12 facilitates tunneling subcutaneously from insertion site 2 to the remote tissue expansion site 3, and at the same time affords protection for the components therewithin. Preferably, but not necessarily, member 12 may have the shape of an elongated cylindrical shell.

FIG. 3 is for illustrative purposes only, and the spaces and dimensions should be ignored. In particular, the member 9 may be placed within the tube 5 and deflated balloon 8, and the assemblage snugly fit within the interior of member 12 so that relative movement between elements 5, 8, 9 and 12 is inhibited during passage of the apparatus 11 from site 2 to site 3. After the balloon 8 has been positioned at the tissue expansion site 3, the inner member 9 may be withdrawn. Withdrawal of member 9 permits tube 5 and deflated balloon 8 to collapse to a certain extent, and thereby permits easy removal of outer member 12 without inadvertently moving tube 5 and balloon 8 from their subcutaneous positions.

FIG. 3 also shows an optional member 13 for releasably holding members 9 and 12 together so that members 9 and 12 move in unison during the subcutaneous passage from site 2 to site 3. After the deflated balloon 8 has been properly positioned at site 3, the optional member 13 may be removed to permit subsequent removal of members 9 and 12.

FIG. 4 shows a transverse cross-sectional view taken along the line 4—4 of FIG. 3.

Figure 5:
FIG. 5 shows a portion of the inflation tube having a special self-sealing coupling device at one end.

An optional alternate embodiment is shown in part in FIG. 5. FIG. 5 shows a portion of inflation tube 5 having a self-sealing coupling device 14 operably connected at one end thereof. The coupling device 14 serves as a self-sealing connection means between the inflation tube 5 and an external device, such as syringe 6, for administering the inflation fluid.

The optional coupling device 14 is particularly useful when there is to be substantially permanent implantation of the inflatable balloon 8, the inflation tube 5 and the coupling device 14 to function as a substantially permanent prosthesis. In such event, the materials from which the balloon 8, tube 5, and coupling device 14 are formed are selected to have appropriate physical, chemical and biological characteristics to facilitate substantially permanent implantation. Such characteristics are selected to avoid and/or minimize body rejection and/or infection. One such characteristic of particular concern is the permeability of the mentioned materials.

While the invention has been described with respect to several preferred embodiments, it will be appreciated that many other variations, modifications and applications of the invention may be made.

What is claimed is:

1. A tissue expander apparatus for use in expanding dermal and epidermal tissue, comprising:
   an inflatable balloon adapted to be passed through subcutaneous tissue from an insertion site to a tissue expansion site which is remote from said insertion site;
   an inflation tube having one end connected to said inflatable balloon and another end serving as an entry port for inflation fluid;
   an elongated firm first member disposed within at least one of said inflation tube and said inflatable balloon and of sufficient rigidity to facilitate passage of said tissue expander apparatus through subcutaneous tissue from said insertion site to said remote tissue expansion site;
   said elongated first member being adapted to be withdrawn from said at least one of said inflation tube and said inflatable balloon after said inflatable balloon has been positioned at said tissue expansion site and prior to inflation of said inflatable balloon by said inflation fluid for expansion of dermal and epidermal tissue at said expansion site;
   a removable elongated second member within which said inflatable balloon, said inflation tube and said elongated first member are disposed; and
   said removable elongated second member being of sufficient rigidity to facilitate tunneling of said tissue expander apparatus through subcutaneous tissue from said insertion site to said remote tissue expansion site and to protect said inflatable balloon and said inflation tube during said subcutaneous tunneling.

2. The apparatus of claim 1, including:
   a coupling device operably connected at said entry port of said inflation tube and functioning as a self-sealing inflation connection means between said inflation tube and an external device for administering said inflating fluid; and
   said inflatable balloon, said inflation tube and said coupling device being formed of predetermined materials, respectively, having physical, chemical and biological characteristics to facilitate substantially permanent implantation of said inflatable balloon, said inflation tube and said coupling device to function as a prosthesis.

3. A tissue expander apparatus for use in expanding dermal and epidermal tissue, comprising:
   an inflatable balloon adapted to be passed through subcutaneous tissue from an insertion site to a tissue expansion site which is remote from said insertion site:
   an inflation tube having one end connected to said inflatable balloon and another end serving as an entry port for inflation fluid;
   an elongated firm first member disposed within at least one of said inflation tube and said inflatable balloon and of sufficient rigidity to facilitate passage of said tissue expander apparatus through subcutaneous tissue from said insertion site to said remote tissue expansion site;
   said elongated first member being adapted to be withdrawn from said at least one of said inflation tube and said inflatable balloon after said inflatable balloon has been positioned at said tissue expansion site and prior to inflation of said inflatable balloon by said inflation fluid for expansion of dermal and epidermal tissue at said expansion site;

a coupling device operably connected at said entry port of said inflation tube and functioning as a self-sealing inflation connection means between said inflation tube and an external device for administering said inflation fluid; and said inflatable balloon, said inflation tube and said coupling device being formed of predetermined materials, respectively, having physical, chemical and biological characteristics to facilitate substantially permanent implantation of said inflatable balloon, said inflation tube and said coupling device to function as a prosthesis.

4. A method of expanding dermal and epidermal tissue, comprising the steps of:

inserting a first device at an insertion site which is remote from a tissue expansion site, said first device being of sufficient rigidity to form in subcutaneous tissue a tunnel extending from the insertion site to the expansion site;

passing said first device subcutaneously through said tunnel from said insertion site to said tissue expansion site;

withdrawing said first device;

inserting a deflated tissue expander device at said insertion site;

passing at least an inflatable portion of said deflated tissue expander device subcutaneously through said tunnel from said insertion site to said tissue expansion site; and at least partially inflating said inflatable portion of said tissue expander device to expand dermal and epidermal tissue at said tissue expansion site.

5. The method of claim 4, wherein:

said inflation step is performed substantially immediately after passing said inflatable portion of said tissue expander device to said tissue expansion site.

6. The method of claim 5, including the step of:

securing at least an inflation part of said tissue expander device near said insertion site.

7. The method of claim 6, including the steps of:

sequentially increasing inflation of said inflatable portion of said tissue expander device until a desired tissue expansion has been obtained.

8. The method of claim 5, including the steps of:

sequentially increasing inflation of said inflatable portion of said tissue expander device until a desired tissue expansion has been obtained.

9. The method of claim 8, including the steps of:

deflating and withdrawing said tissue expander device after said desired tissue expansion inflation has been obtained; and thereafter utilizing the expanded tissue as desired.

10. The method of claim 4, including the step of:

securing at least an inflation part of said tissue expander device near said insertion site.

11. The method of claim 10, including the steps of:

sequentially increasing inflation of said inflatable portion of said tissue expander device until a desired tissue expansion has been obtained.

12. The method of claim 4, including the steps of:

sequentially increasing inflation of said inflatable portion of said tissue expander device until a desired tissue expansion has been obtained.

13. The method of claim 12, including the steps of:

deflating and withdrawing said tissue expander device after said desired tissue expansion has been obtained; and thereafter utilizing the expanded tissue as desired.

14. The method of claim 12, including the step of:

retaining the inflated tissue expander device substantially permanently in place to function as a prosthesis.

15. The method of claim 4, including the step of:

retaining the inflated tissue expander device substantially permanently in place to function as a prosthesis.

16. A method of expanding dermal and epidermal tissue, comprising the steps of:

inserting at an insertion site which is remote from a tissue expansion site a tissue expander assembly comprising a deflated tissue expander device and one or more removable members of sufficient rigidity for passing the deflated tissue expander device through subcutaneous tissue between the insertion site and the expansion site;

passing said deflated tissue expander assembly through subcutaneous tissue from said insertion site to said tissue expansion site;

withdrawing said one or more removable members; and at least partially inflating an inflatable portion of said tissue expander device to expand dermal and epidermal tissue at said tissue expansion site.

17. The method of claim 16, including the steps of:

sequentially increasing inflation of said inflatable portion of said tissue expander device until a desired tissue expansion has been obtained; and thereafter deflating and withdrawing said tissue expander device.

18. The method of claim 16, including the steps of:

sequentially increasing inflation of said inflatable portion of said tissue expander device until a desired tissue expansion has been attained; and retaining the inflated tissue expander device in place substantially permanently to function as a prosthesis.

* * * * *